US007807655B2

(12) United States Patent
Hedding-Eckerich

(10) Patent No.: US 7,807,655 B2
(45) Date of Patent: Oct. 5, 2010

(54) USE OF PYRIMIDINE NUCLEOTIDES FOR THE TREATMENT OF AFFECTIONS OF THE PERIPHERAL NERVOUS SYSTEM

(75) Inventor: Monika Hedding-Eckerich, Kaarst (DE)

(73) Assignee: Trommsdorff GmbH & Co. KG Arzneimittel, Alsdorf (DE)

( * ) Notice: Subject to any disclaimer, the term of this patent is extended or adjusted under 35 U.S.C. 154(b) by 1167 days.

(21) Appl. No.: 10/511,026

(22) PCT Filed: Apr. 10, 2003

(86) PCT No.: PCT/DE03/01203

§ 371 (c)(1),
(2), (4) Date: May 31, 2005

(87) PCT Pub. No.: WO03/086417

PCT Pub. Date: Oct. 23, 2003

(65) Prior Publication Data

US 2005/0222078 A1  Oct. 6, 2005

(30) Foreign Application Priority Data

Apr. 10, 2002 (DE) .................................. 102 15 753

(51) Int. Cl.
*A01N 43/04* (2006.01)
*A61K 31/70* (2006.01)

(52) U.S. Cl. ............................. 514/49; 514/43; 514/50; 514/51

(58) Field of Classification Search .................... None
See application file for complete search history.

(56) References Cited

FOREIGN PATENT DOCUMENTS

WO    WO 03/086417    10/2003

OTHER PUBLICATIONS

Navarro et al. BioFactors (1999), vol. 10, pp. 67-76.*
Connolly et al. TIPS (1999), vol. 20, pp. 218-225.*
International Preliminary Examination Report, PCT/DE03/01203, Jul. 19, 2004.
Wattig, B., et al. Nucleotides Accelerate Regeneration of Nerves. Zeitschrift Fuer Klinische Medizin (Berlin). vol. 46, No. 19, 1991, pp. 1371-1373.
Wattig, B., et al., Acceleration of Muscle Regeneration by Nucleotide Administration Experimental Morphometric Studies, Zentralblatt Fur Pathologie, Germany 1991, vol. 137, No. 5, 1991, pp. 409-413.
Wattig, B., et al., Acceleration of Nerve and Muscle Regeneration by Administration of Nucleotides—electroneurohphysiological and Morphometrical Investigations, ACTA Histochchemica, Supplementband, Germany 1992, vol. 42. 1992. pp. 333-339.
International Search Report, PCT/DE03/01203, Aug. 21, 2003.

* cited by examiner

*Primary Examiner*—Patrick T Lewis
(74) *Attorney, Agent, or Firm*—Turocy & Watson, LLP

(57) ABSTRACT

The invention relates to the use of a pyrimidine nucleotide for treating affections of the peripheral nervous system, particularly polyneuropathies, neuritides, and myopathies, and the use thereof for stimulating the regeneration of nerves.

16 Claims, No Drawings

USE OF PYRIMIDINE NUCLEOTIDES FOR THE TREATMENT OF AFFECTIONS OF THE PERIPHERAL NERVOUS SYSTEM

The invention relates to the use of a pyrimidine nucleotide for the treatment of affections of the peripheral nervous system, particularly of polyneuropathies, neuritides and myopathies as well as the use for the stimulation of the regeneration of nerves.

Affections of nerves represent events, which are ranked at first position in traumatology, but occur also attendant on inflammatory, metabolic, endocrine, vascular and toxic based diseases.

Scientific insights let assume, that axons are of importance for the efficiency of peripheral nerves, as they seem to be important for the transport and conductibility of supply substances and information.

In the case of an affection of nerves with transection of nerve tracts, a sprouting of axons begins in the lesion area and a form of an own repair system can be observed in the nerve, which leads to the regeneration of nerves in the case of polyneuropathy, for example.

Experimentally three phases were recognized in the repair system.

1. A latency phase from the 1. to 2. day after the trauma.

The axon degenerates at the location of the lesion. Fragmentation takes place. Also the myelin of the covering tissue is included by this process and decomposes within approximately 8 days.

2. A regeneration phase from the 2. to 12. day.

At the proximal and distal stump of the transected nerve area the Schwann cells divide themselves. A young axon sprouts out and accumulates proteins, lipids and RNA. Bungner bands are trying to rebuild the connection between the transected filament pieces. The young axon migrates along this lead.

3. A maturation phase from the 12. to 90. day.

The new nerve filament advances in thickness due to myelinisation. New cell structures are built.

Certain substrates such as cytidine and uridine are needed, which take effect as energy contributors, so that this repair system can operate. Nucleic acids represent the basis of nerve regeneration. Nucleosides are incorporated by the nerve cells and converted into nucleotides. Nucleotides get into the axons, which are decisively participating in the regeneration process. Cytidine and uridine effect thereby the new synthesis of structure components of the nerve cell (J. Cervos-Navarro, Ärzte Zeitung, 1992, No. 131, p. 2).

In clinical studies on patients with a polyneuropathy the external application of a mixture of cytidine and uridine led to an amelioration of the typical symptoms of polyneuropathy.

A study on Wistar rats proved the good effectiveness of the active agent combination of uridine monophosphate (UMP) and cytidine monophosphate (CMP) with respect to the regeneration of traumatically affected peripheral nerves.

In this test series a group of test animals was administered UMP, another group CMP and a further group a mixture of UMP and CMP. Only the group, which received the active agent combination of UMP and CMP showed a magnified filament area on the basis of expanded myeline sheath areas. The structural analysis of the nerve filaments proved, that in the UMP/CMP group a clear magnification of the average filament area occurred, which was in consequence of the magnified myelin and axon areas.

The test animals, which received only the individual substances UMP or CMP, showed no comparable results (B. Wattig et al., Zeitschrift für klinische Medizin, 1991, 46, 1371-1373).

The objective of the present invention is to provide physiologically well acceptable substances, which can be used for the treatment of affections of the peripheral nervous system as well as for the stimulation of the regeneration of nerves.

This object is solved by the technical teaching of the independent claim 1. Further advantageous features, aspects and details of the invention are evident from the dependent claims, the description and the examples.

Surprisingly it was found, that for the treatment of affections of the peripheral nervous system as well as for the stimulation of the regeneration of nerves an active agent combination of at least 2 pyrimidine nucleotides is not needed, but the individual substances show an outstanding effect.

Contrary to the above mentioned insights from the animal test study, which deny the individual substances UMP and CMP an effectivity in the treatment of affections of the peripheral nervous system and in the regeneration of nerves, respectively, it could be proven, that UMP as well as CMP exhibit a high effectiveness in the case of this indication.

Thus, the invention relates to the use of a single pyrimidine nucleotide for the treatment of affections of the peripheral nervous system and/or the stimulation of the regeneration of nerves. As examples for affections of the peripheral nervous system can be considered polyneuropathies, neuritides and myopathies.

Preferred indications are degenerative diseases of the spinal column, diabetic polyneuropathies, polyneuropathies after alcohol abusus, other toxic polyneuropathies, facial nerve paresis, face neuralgias, multiple sclerosis, root neuritides, cervical, syndrome, shoulder-arm syndrome, ischialgia, lumbago, intercostal neuralgia, trigeminus neuralgia as well as herpes zoster.

As pyrimidine nucleotides are preferably suitable uridine-5'-monophosphate, uridine-5'-diphosphate, uridine-5'-triphosphate, cytidine-5'-monophosphate, cytidine-5'-diphosphate or cytidine-5'-triphosphate. Especially suitable among these uridine phosphates and cytidine phosphates for the use according to invention are UMP and CMP, whereas UMP is to be preferred to CMP.

The pyrimidine nucleotide is administered in a daily dose rate of 1-100 mg, preferably of 5-50 mg, more preferably of 7-40 mg and most preferably of 10-35 mg.

Another use of a pyrimidine nucleotide is the manufacture of a pharmaceutical composition, which is suitable for the treatment of affections of the peripheral nervous system and/or for the stimulation of the regeneration of nerves.

Such pharmaceutical compositions can contain beside the pyrimidine nucleotide the common solid or liquid substrates, diluents or solvents and the commonly used pharmaceutical adjuvants, respectively. The pharmaceutical compositions are manufactured in a known manner with an active agent concentration of pyrimidine nucleotide of 1-100 mg, preferably of 5-50 mg, more preferably of 7-40 mg and most preferably of 10-35 mg according to the desired application type.

The pyrimidine nucleotides applicable according to invention as well as the pharmaceutical compositions applicable according to invention are suitable for an intravenous, intraperitoneal, intramuscular, subcutaneous, rectal, vaginal, transdermal, topical, intradermal, intestinal, oral, intragastric, intracutaneous, intranasal, intrabuccal, percutaneous, sublingual or any other application.

The preferred pharmaceutical compositions consist in an administration form, which is suitable for an oral application. Such administration forms are for example tablets, film tablets, coated tablets, capsules, pills, powders, solutions, dispersions, suspensions, deposits or inhalation solutions.

Adequate tablets can be obtained for example by admixing a pyrimidine nucleotide with known adjuvants such as inert dilutors like dextrose, sugar, sorbitol, mannite, polyvinylpyrrolidone, disintegrating agents like corn starch or alginic acid, binders like starch or gelatin, lubricants like magnesium stearate or talc and/or agents for achieving a deposit effect like carboxypolymethylene, carboxymethylcellulose, cellulose acetate phthalate or polyvinyl acetate. The tablets can also consist of several layers.

Accordingly coated tablets can be manufactured by coating of cores manufactured analogously to the tablets with commonly used agents in tablet coating such as polyvinylpyrrolidone or shellac, gum arabic, talc, titan dioxide or sugar. Thereby also the coating can consist of several layers, whereas the adjuvants can be used mentioned above with the tablets.

Solutions or suspensions with the active agent applicable according to invention can additionally contain taste enhancing agents such as saccharine, cyclamate or sugar as well as aroma agents such as vanillin or orange extract. Moreover they can contain suspension adjuvants such as sodium carboxymethylcellulose or preservative agents such as p-hydroxybenzoate. Capsules containing active agents can be manufactured for example by admixing the active agent with an inert carrier such as lactose or sorbitol and encapsulating it into gelatin capsules.

A preferred composition contains for example sodium citrate dihydrate, water-free citric acid, magnesium stearate, highly disperse silica, mannite, gelatin and if required colorants.

Suitable suppositories can be manufactured by for example admixing with therefor provided substrates such as neutral fats or polyethylene glycol and derivatives thereof, respectively.

Of course parenteral formulations such as injection or infusion solutions can be also taken into consideration. For the parenteral application are especially suitable injection solutions of a pyrimidine nucleotide in physiological sodium chloride solution.

Methods of manufacturing various formulations as well as the different application methods are known to the one skilled in the art and described in detail for example in "Remington's Pharmaceutical Sciences, Mack Publishing Co., Easton Pa.".

EXAMPLES

In the following the effectivity of pyrimidine nucleotides for the treatment of affections of the peripheral nervous system as well as for the stimulation of the regeneration of nerves is described by example of uridine-5'-monophosphate (UMP) by example of the indication lumbago.

80 female as well as male patients, aged between 20 and 63 years, were separated randomly into two groups, one was treated with UMP and the other with placebo.

The treatment ranged over four consecutive days, whereas the treatment could be terminated ahead of schedule as soon as the symptoms were ameliorating in a way, that a further treatment was needless.

Applied was once per day into a vein of the arm an injection solution of 19.349 mg UMP (this corresponds to a mass of 12.834 mg uridine) in 250 ml of physiological sodium chloride solution over a time period of 30 minutes. The comparison group received as placebo only the 250 ml of physiological sodium chloride solution without an active agent.

For this clinical study only patients were chosen with a pain intensity of at least 40 mm on the VAS scale (VAS: visual analogue scale).

The pain intensity is given on the linear VAS scale in the unit "mm" and was determined by prompting the patients to mark on the linear VAS scale the point, which corresponded to their respective pain intensity. Thereby a non sensible pain was given with the value 0 mm and the possibly maximum pain with the value 100 mm.

The pain intensity of the patients was continuously checked, whereas the patients also had to indicate the respective duration of the single pain periods.

Results

Already within the initial 24 h after the first injection a clear decrease in pain can be observed in the case of the UMP patients compared to the patients having received only a placebo (see table I).

Table I proves, that already after a short time period after the initial injection the pain intensity strongly decreases in the resting and moving state in the case of the UMP patient group. The finger-floor distance represents a measure for the mobility, i.e. for the grade of capability to bend the back, and is given in the unit "cm", whereas the distance between the finger tip in the case of outstretched arms and the curvature in the case of maximal possible bending of the back was measured.

TABLE I average values of the UMP and placebo patient group

|  | UMP Base line | 24 h after inj. | Placebo Base line | 24 h after inj. |
|---|---|---|---|---|
| Pain during resting state (mm) | 60.3 | 46.2 | 63.5 | 53.6 |
| Pain during movement (mm) | 76.1 | 56.9 | 76.3 | 65.1 |
| Daily duration of pain (h) | 15.8 | 10.7 | 14.8 | 11.7 |
| Presence of myogelosis | 100% | 90% | 100% | 100% |
| Finger-floor distance (cm) | 43.8 | 32.5 | 46.8 | 38.3 |

Table II emphasizes the differences in the decrease of pain intensity in the comparison of the UMP and placebo patient group.

TABLE II decrease of pain in the case of the UMP and placebo patient group

|  | Δ UMP | Δ Placebo | Δ UMP − Δ Placebo |
|---|---|---|---|
| Pain during resting state (mm) | −12.8 | −9.4 | −3.4 |
| Pain during movement (mm) | −17.9 | −11.1 | −6.8 |
| Daily duration of pain (h) | −4.3 | −2.9 | −1.4 |
| Finger-floor distance (cm) | −10.1 | −7.4 | −2.7 |

Table II proves the clearly better decrease in pain in the case of the UMP patient group in comparison to the placebo patient group. During the further three days it could be observed, that the differences for the decrease in pain as well as for the daily duration of pain as well as for the finger-floor distance of the UMP patient group (Δ UMP) slowly converged to the differences of the placebo patient group (Δ Placebo), whereas however the absolute values of the above-mentioned test parameters in the case of the UMP patient group were always below the corresponding absolute values for the placebo group.

Thus the carried out clinical study proves clearly the pharmaceutical effectivity of an individually administered pyrimidine nucleotide and the view held until now in the scientific literature, that only combinations of pyrimidine nucleotides achieve an appropriate effect, is therewith disproved.

The invention claimed is:

1. A method of using uridine-5'-monophosphate or cytidine-5'-monophosphate for the treatment of affections of the peripheral nervous system and/or for the stimulation of the regeneration of nerves, consisting of administering uridine-5'-monophosphate or cytidine-5'-monophosphate to a patient in need thereof.

2. The method according to claim 1, wherein uridin-5'-monophosphate wherein uridine-5'-monophosphate is administered to a patient in need thereof.

3. The method according to claim 1, wherein the affections of the peripheral nervous system concern polyneuropathies, neuritides and/or myopathies.

4. The method according to claim 3, wherein the polyneuropathies, neuritides and myopathies concern degenerative diseases of the spinal column, diabetic polyneuropathies, polyneuropathies after alcohol abusus, other toxic polyneuropathies, facial nerve paresis, face neuralgias, multiple sclerosis, root neuritides, cervical syndrome, shoulder-arm syndrome, ischialgia, lumbago, intercostals neuralgia, trigeminus neuralgia and/or herpes zoster.

5. The method according to claim 1, wherein uridine-5'-monophosphate or cytidine-5'-monophosphate is administered in a daily dose rate of 1-100 mg.

6. A method of using uridine-5'-monophosphate or cytidine-5'-monophosphate for the manufacture of a pharmaceutical composition for the treatment of affections of the peripheral nervous system and/or for the stimulation of the regeneration of nerves, comprising adding uridine-5'-monophosphate or cytidine-5'-monophosphate to a pharmaceutical composition, wherein uridine-5'-monophosphate is contained in a concentration of 1-40 mg, or cytidine-5'-monophosphate is contained in a concentration of 1-100 mg.

7. Pharmaceutical composition consisting of uridine-5'-monophosphate or cytidine-5'-monophosphate as pharmaceutically active ingredient optionally together with physiologically acceptable carriers, adjuvants and/or diluents, wherein uridine-5'-monophosphate is contained in a concentration of 1-40 mg, or cytidine-5'-monophosphate is contained in a concentration of 1-100 mg.

8. Pharmaceutical composition according to claim 7, wherein the pharmaceutical composition is suitable for oral application or injection.

9. The method according to claim 2, wherein the affections of the peripheral nervous system concern polyneuropathies, neuritides and/or myopathies.

10. The method according to claim 9, wherein the polyneuropathies, neuritides and myopathies concern degenerative diseases of the spinal column, diabetic polyneuropathies, polyneuropathies after alcohol abusus, other toxic polyneuropathies, facial nerve paresis, face neuralgias, multiple sclerosis, root neuritides, cervical syndrome, shoulder-arm syndrome, ischialgia, lumbago, intercostals neuralgia, trigeminus neuralgia and/or herpes zoster.

11. The method according to claim 2, wherein uridine-5'-monophosphate or cytidine-5'-monophosphate is administered in a daily dose rate of 1-100 mg.

12. The method according to claim 3, wherein uridine-5'-monophosphate or cytidine-5'-monophosphate is administered in a daily dose rate of 1-100 mg.

13. The method according to claim 4, wherein uridine-5'-monophosphate or cytidine-5'-monophosphate is administered in a daily dose rate of 1-100 mg.

14. The method according to claim 9, wherein uridine-5'-monophosphate or cytidine-5'-monophosphate is administered in a daily dose rate of 1-100 mg.

15. The method according to claim 10, wherein uridine-5'-monophosphate or cytidine-5'-monophosphate is administered in a daily dose rate of 1-100 mg.

16. Pharmaceutical composition according to claim 7, wherein the pharmaceutical composition is suitable for oral application or injection.

* * * * *